United States Patent
Govari

(10) Patent No.: US 11,564,702 B2
(45) Date of Patent: Jan. 31, 2023

(54) SHAPE MEMORY ELEMENT FOR STRAIGHTENING MALLEABLE DEVICE

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 373 days.

(21) Appl. No.: 16/427,854

(22) Filed: May 31, 2019

(65) Prior Publication Data
US 2020/0375618 A1    Dec. 3, 2020

(51) Int. Cl.
*A61B 17/24* (2006.01)
*A61B 17/00* (2006.01)

(52) U.S. Cl.
CPC .... *A61B 17/24* (2013.01); *A61B 2017/00017* (2013.01); *A61B 2017/00305* (2013.01); *A61B 2017/00526* (2013.01); *A61B 2017/00867* (2013.01); *A61B 2017/00946* (2013.01)

(58) Field of Classification Search
CPC .......... A61B 17/24; A61B 2017/00017; A61B 2017/00305; A61B 2017/00526; A61B 2017/00867; A61B 2017/00946; A61B 2034/2051; A61B 2034/2072; A61B 2217/005; A61M 1/84; A61M 2205/0266; A61M 2205/0272
See application file for complete search history.

(56) References Cited

U.S. PATENT DOCUMENTS

| | | | |
|---|---|---|---|
| 4,665,906 A | 5/1987 | Jervis | |
| 4,977,886 A * | 12/1990 | Takehana | A61B 1/0058 600/151 |
| 6,080,160 A * | 6/2000 | Chen | A61N 5/0601 606/151 |
| 7,520,876 B2 * | 4/2009 | Ressemann | A61B 17/24 604/510 |
| 2007/0073312 A1 * | 3/2007 | Mykleby | A61M 1/84 606/113 |
| 2007/0239138 A1 * | 10/2007 | Lawrence | A61B 1/012 604/531 |

(Continued)

FOREIGN PATENT DOCUMENTS

EP    1072280    1/2001

OTHER PUBLICATIONS

International Search Report dated Jul. 20, 2020 from corresponding PCT/IB2020/054415 Patent Application.

(Continued)

*Primary Examiner* — Mohamed G Gabr
(74) *Attorney, Agent, or Firm* — Frost Brown Todd LLP

(57) ABSTRACT

A medical tool includes a handle, a tubular member, and a bendable shape memory element (SME). The tubular member is attached to and extends from the handle and is configured to be inserted into an orifice of a patient. The tubular member has a distal-end section that is configured to be bent so as to perform a medical procedure in the orifice. The bendable shape memory element (SME) is coupled to the distal-end section of the tubular member, wherein the SME is configured to straighten when heated into a preformed shape, thereby straightening the distal-end section.

20 Claims, 3 Drawing Sheets

(56) References Cited

U.S. PATENT DOCUMENTS

| | | | |
|---|---|---|---|
| 2008/0172033 A1* | 7/2008 | Keith | A61B 1/233 |
| | | | 604/117 |
| 2008/0200761 A1 | 8/2008 | Schwartz et al. | |
| 2010/0312101 A1* | 12/2010 | Drontle | A61M 25/0113 |
| | | | 606/196 |
| 2014/0150782 A1 | 6/2014 | Vazales et al. | |
| 2019/0009054 A1 | 1/2019 | Bishawi | |

OTHER PUBLICATIONS

U.S. Appl. No. 62/741,402, filed Oct. 4, 2018, entitled "Malleable Suction Device".

\* cited by examiner

SHAPE MEMORY ELEMENT FOR STRAIGHTENING MALLEABLE DEVICE

FIELD OF THE INVENTION

This invention relates generally to medical tools, and specifically to a rigid ear, nose, and throat (ENT) tool having an adjustable shape.

BACKGROUND OF THE INVENTION

Various surgical tools were proposed in the patent literature for facilitating treatment that may require adjusting a shape of the tool. For example, U.S. Patent Application 2014/0150782, issued as U.S. Pat. No. 10,004,863 on Jun. 26, 2018, describes a closed suction system module comprising a coupling member configured to couple to a suction port of a multi-port manifold or endotracheal tube adapter. In one embodiment, the closed suction system module comprises a suction catheter configured to clean the interior surfaces of body-inserted tubes orartificial airways (alone or in addition to suctioning natural airways or portions of the respiratory tract). The suction catheter may comprise a cleaning portion at a distal portion of the suction catheter (e.g., near the distal end or tip of the suction catheter). In an embodiment, the distal end of the suction catheter can comprise one or more flexible materials that aid in the steerabilty of the catheter.

As another example, U.S. Pat. No. 4,665,906 describes medical devices which are currently proposed to use elements made from shape memory alloys that may be improved by the use of stress-induced martensite alloy elements instead. The use of stress-induced martensite decreases the temperature sensitivity of the devices, thereby making them easier to install and/or remove. In an embodiment, a catheter device is straightened by insertion of a straight pin down the catheter axis, the catheter deforming by the formation of stress-induced martensite.

U.S. Patent Application 2008/0200761, issued as U.S. Pat. No. 8,231,524 on Jul. 31, 2012, describes an endoscope device having a curvable portion and a pivotable lever enclosed within a housing. The lever is connected to a spring means for returning a trigger and the control wire to a resting position once a user is finished squeezing the trigger. The pivotable lever defines first and second ends connected to an adjustment wire and a control wire respectively. When the trigger is squeezed the curvable portion curves in a controlled manner from a fully straight configuration.

SUMMARY OF THE INVENTION

An embodiment of the present invention provides a medical tool including a handle, a tubular member, and a bendable shape memory element (SME). The tubular member is attached to and extends from the handle and is configured to be inserted into an orifice of a patient. The tubular member has a distal-end section that is configured to be bent so as to perform a medical procedure in the orifice.

The bendable shape memory element (SME) is coupled to the distal-end section of the tubular member, wherein the SME is configured to straighten when heated into a pre-formed shape, thereby straightening the distal-end section.

In some embodiments, the SME is made at least partially from a shape-memory material whose pre-formed shape straightens the SME.

In some embodiments, the shape-memory material includes Nitinol.

In an embodiment, the SME is configured to receive an electrical current via wiring running through the tubular member and to be straightened in response to the electrical current. In another embodiment, the SME is configured to be heated by conducting the electrical current provided thereto, so as to revert to the straightened pre-formed shape.

In an embodiment, the medical tool further includes a heater, which is thermally coupled to the SME, and which is configured to be heated by conducting the electrical current provided thereto, so as to straighten the SME to the straightened pre-formed shape.

In some embodiments, the SME is adhered to an interior or exterior of a wall of the tubular member. In other embodiments, the SME is incorporated into a wall of the tubular member.

In an embodiment, the SME includes a sleeve configured to surround the distal-end section.

There is additionally provided, in accordance with an embodiment of the present invention, a method for manufacturing a medical instrument, the method including attaching to and extending from a handle a tubular member that is configured to be inserted into an orifice of a patient, the tubular member having a distal-end section that is configured to be bent so as to perform a medical procedure. A bendable shape memory element (SME) is coupled to the distal-end section of the tubular member, wherein the SME is configured to straighten when heated into a pre-formed shape, thereby straightening the distal-end section.

There is additionally provided, in accordance with an embodiment of the present invention, a method, including inserting into an orifice in a patient body a medical tool, which includes (a) a handle, (b) a tubular member, attached to and extending from the handle, the tubular member having a distal-end section that is configured to be bent so as to perform a medical procedure in the orifice, and (c) a bendable shape memory element (SME) coupled to the distal-end section of the tubular member, wherein the SME is configured to straighten when heated into a pre-formed shape, thereby straightening the distal-end section. The distal end of the tubular member is bent from the handle. The medical procedure is performed in the orifice while the SME is bent. After performing the medical procedure, the distal-end section of the tubular member is straightened by setting the SME to the pre-formed shape. The straightened medical tool is retracted from the patient body.

The present invention will be more fully understood from the following detailed description of the embodiments thereof, taken together with the drawings in which:

DETAILED DESCRIPTION OF EMBODIMENTS

Overview

Figure 1:
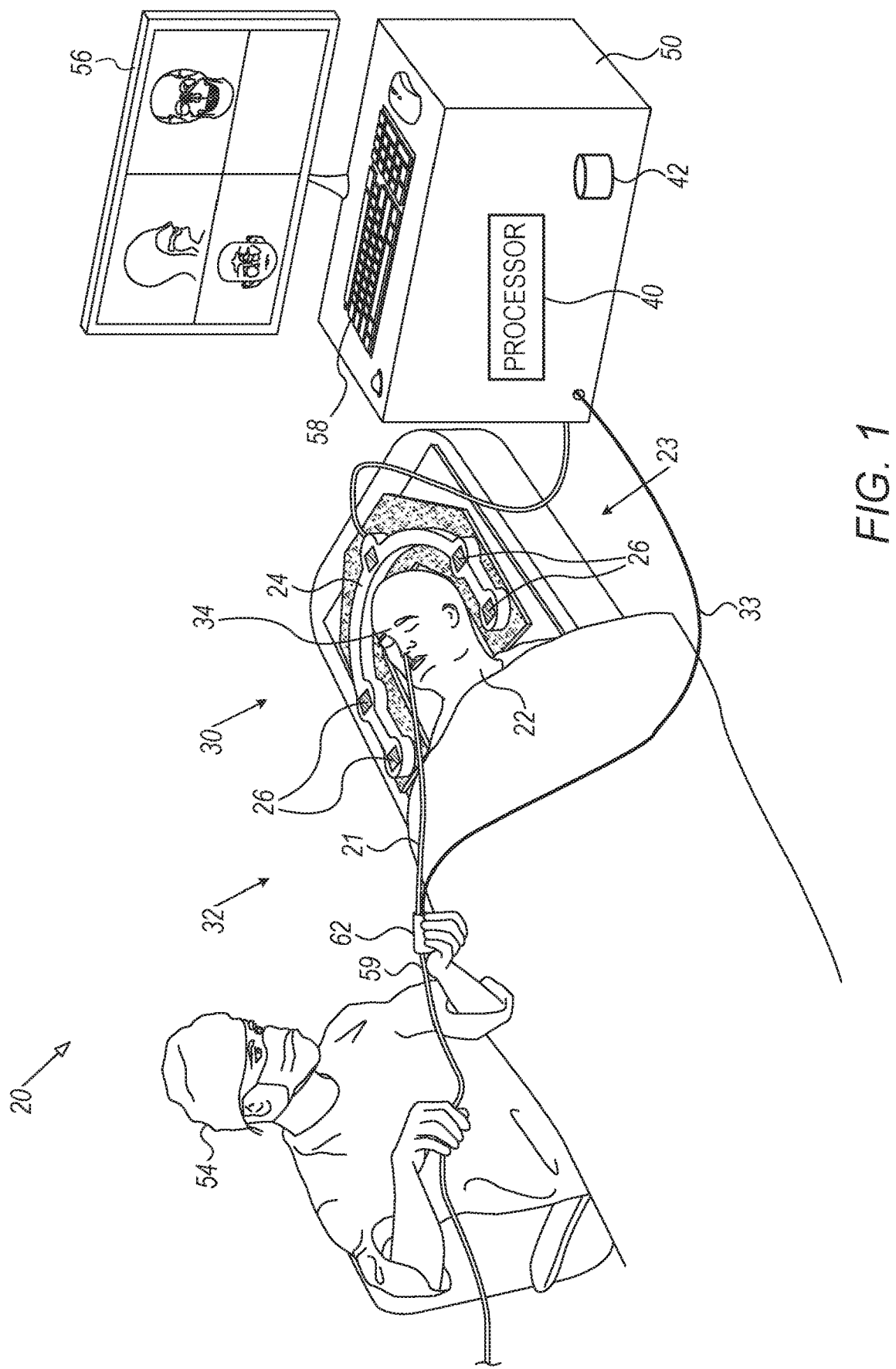
FIG. 1 is a schematic, pictorial illustration of an ear, nose, and throat (ENT) system, according to an embodiment of the present invention.

Some cavities of an organ, such as the nasal sinuses, are complicated three-dimensional structures that vary from person to person. Achieving access to a particular sinus, and to a selected region of the sinus, may require a rigid medical tool having a very specific shape. Medical tools, such as surgical tools for sinus treatments, e.g., endoscopes, graspers, and/or suction devices, are produced in a variety of shapes which are typically available to an ear, nose, and throat (ENT) physician. Thus, an operating ENT physician is able to choose the particular shape that is best suited to a specific task within the sinuses. However, in order to retract such tool, the physician may need to satisfactorily straighten a distal end of the tool.

Embodiments of the present invention provide improved medical tools and associated methods, which enable straightening of a shaped medical tool that is still rigid enough to be suitable for its intended use. In the disclosed embodiments, a medical tool comprises a bendable shape memory element (SME) made of shape memory material. The SME comprises, or is coupled to, an electrical heating mechanism that allows the shape memory material to be heated above a predetermined temperature. The SME is configured so that it is flexible in its unheated state, and rigid and straight in its pre-formed state (i.e., when heated) so as to straighten the distal end of the tool.

In the present context, the term "shape-memory material" refers to any material that has a pre-formed shape and returns to its pre-deformed shape when heated.

There are many types of shape memory materials that are manipulated by temperature, ranging from metal alloys to polymers. The embodiments described herein refer mainly to shape memory alloys, and more particularly to Nitinol, but the disclosed tool can be implemented using any other suitable shape-memory material.

In some embodiments, electrical current passes through the SME structure itself, causing the SME to heat due its own electrical resistance. In other embodiments, the electrical current passes through one or more heaters fitted (e.g., attached) to the SME.

The SME may come in a form of a spring, a beam, or a cylinder, among other shapes. Such elements may be disposed internally, e.g., inside a portion of the distal end of the tool. Alternatively or additionally, such elements may be in the form of an external sleeve put over a portion of a distal end of a tubular member of the medical tool, and/or incorporated into a wall of the distal end.

For example, in an embodiment, to straighten a bent distal end of an ENT tool, such as a suction device, a flexible tubular nitinol spring is placed over a portion of a distal end of the device. The spring is then heated to 60° C. so that it returns to its pre-deformed shape and straightens the distal end of the suction device. The disclosed technique for straightening a medical tool using an element made of shape-memory material may simplify minimally invasive medical procedures.

System Description

FIG. 1 is a schematic, pictorial illustration of an ear, nose, and throat (ENT) system 20, according to an embodiment of the present invention. System 20 is operated by a system processor 40 communicating with one or more memories 42. In the following description, system 20 comprises a rigid tool 21 which a physician 54 is assumed to use to perform a nasal sinus procedure on a patient 22, as is described in more detail below. Tool 21 comprises a magnetic sensor 32 that is tracked during the procedure by a magnetic tracking system 23. For the tracking to be effective, a medical image of patient 22 and of magnetic tracking system 23 are registered in system 20's frames of reference. The medical image may typically comprise a magnetic resonance imaging (MRI) image or a fluoroscopic image, whereas in the description herein the image is assumed to comprise, by way of example, a fluoroscopic computerized tomography (CT) image.

Prior to and during the sinus procedure, a magnetic radiator assembly 24 within in the magnetic tracking system is positioned beneath the patient's head. Assembly 24 comprises magnetic field radiators 26 which are fixed in position and which transmit alternating sinusoidal magnetic fields into a region 30 where the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention.

Elements of system 20, including radiators 26, are controlled by system processor 40. Processor 40 may be mounted in a console 50, which comprises operating controls 58 that typically include a keypad and/or a pointing device such as a mouse or trackball. Console 50 connects to the radiators via a cable and/or wirelessly. Physician 54 uses operating controls 58 to interact with the processor while performing the ENT procedure using system 20. While performing the procedure, the processor may present results of the procedure on a screen 56.

Tool 21 comprises a handle 62 at its proximal end and a distal tip 61 at its distal end. Handle 62 is connected to a hose 59 that enables performing with tool 21 procedures such as suction, as described below. As further seen, handle 62 is connected to console 50 with a cable 33 to supply electrical current to straighten tool 21 using an SME on a distal end of tool 21, as described below.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 further uses the software, inter alia, to operate magnetic radiators 26 of assembly 24. As stated above, the radiators transmit sinusoidal alternating magnetic fields of different frequencies into region 30, including the head of patient 22, and the fields from the radiators induce signals in sensor 32. The signals, and/or data derived from the signals, may be transmitted by wire and/or wirelessly to the processor which analyzes the received data and/or signals to derive location and orientation values, measured with respect to a frame of reference defined by the assembly, for the sensors. In the description herein rigid tool 21 is assumed to be a suction device, used for permitting drainage of fluid through a lumen of the device. Those having skill in the art will be able to adapt the description, mutatis mutandis, for other types of ENT tools, such as an endoscope or a grasper, and all such tools are assumed to be comprised within the scope of the present invention.

Shape Memory Element for Straightening a Malleable Device

Figure 2A:
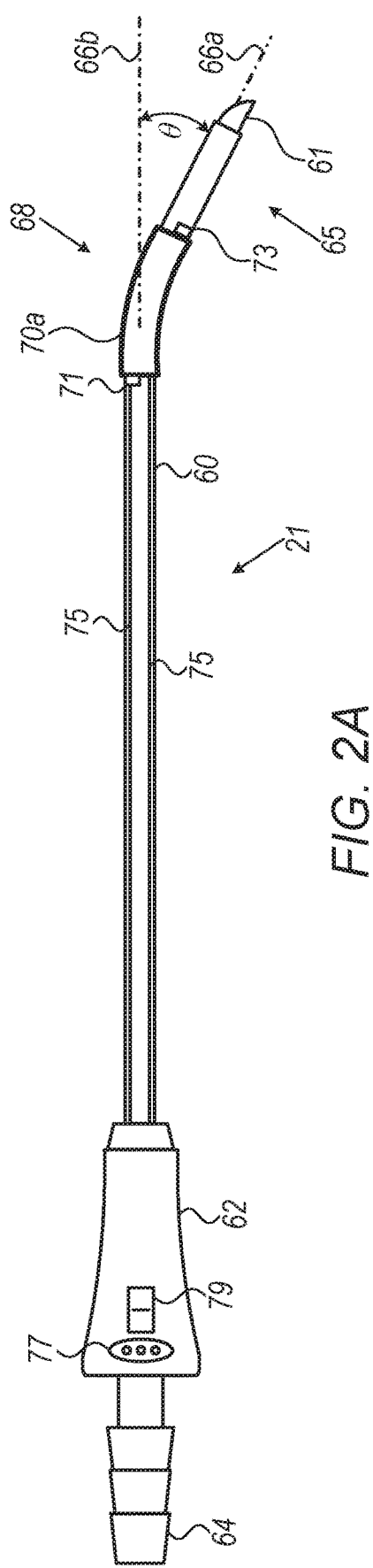
FIGS. 2A and 2B are schematic diagrams of a rigid tool in a bent state and in a straightened state, respectively, according to an embodiment of the present invention.
Figure 2B:
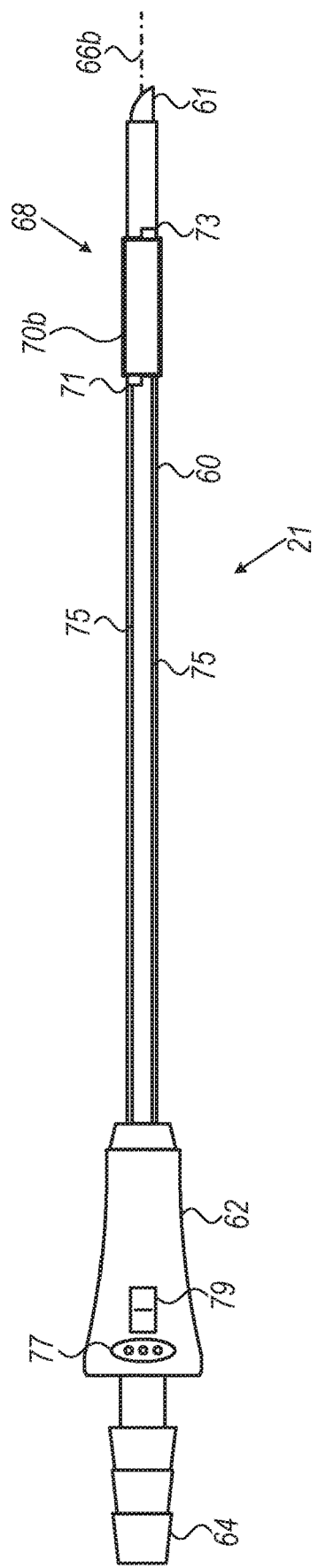

FIGS. 2A and 2B are schematic diagrams of rigid tool in a bent state and in a straightened state, respectively, according to an embodiment of the present invention. Tool 21 comprises a tubular member 60 comprising, at its distal end, a suction tip 65 that can be bent by methods known in the art. In its bent form, shown in FIG. 2A, suction tip 65 defines a longitudinal axis 66a. The suction tip typically makes a non-orthogonal angle θ with a straightened longitudinal axis 66b of member 60, and in one embodiment angle θ is approximately 40°.

At its proximal end, tubular member 60 is connected to handle 62. Handle 62 comprises a hose coupling 64, enabling hose 59 (not shown in FIGS. 2A and 2B, but shown schematically in FIG. 1 above) to be connected to the handle for the purpose of receiving drained fluid from member 60 when suction is applied. In some embodiments, handle 62 may incorporate a control allowing the physician to control the suction through member 60.

An ENT suction device that can be bent manually into a desired shape by a physician is described in U.S. Provisional Patent Application 62/741,402, filed Oct. 4, 2018, entitled "Malleable Suction Device," which is assigned to the assignee of the present patent application and whose disclosure is incorporated herein by reference. In some embodiments, tool 21 comprises an SME 68 fitted between member 60 and tip 65. As seen in FIG. 2A, in its unheated state, SME 68 is flexible enough to be bent into a bent shape 70a.

In some embodiments, SME 68 is made of Nitinol. The disclosed technique can use other material families of shape memory alloys, for example copper-aluminum-nickel. The disclosed technique can also use other types of thermally-responsive materials, such as shape-memory polymers. The shape-memory material may have more than two pre-formed shapes. The description that follows refers to Nitinol as the shape-memory material, by way of example.

Shape memory alloys typically have two stable phases: the high-temperature phase, called "austenite," and the low-temperature phase, called "martensite." Upon heating the shape memory alloy to a temperature above its austenite temperature, the alloy transforms from being a self-accommodated martensite into an austenite with a certain pre-formed shape. Upon cooling the shape memory alloy to a temperature below its martensite temperature, the alloy transforms back into its martensite state.

As SME 68 is heated above its austenitic temperature, SME 68 straightens into its pre-formed shape 70b and by doing so straightens tip 65 (also referred to as the distal end of member 60) as shown in FIG. 2B. By SME 68 being straightened at will by physician 54, suction tip 65 is straightened, as seen in FIG. 2B, and physician 54 can retract straightened tool 21.

In some embodiments, the electrical current passes through SME 68 itself, causing SME 68 to heat due its own electrical resistance. In an alternative embodiment, the electrical current passes through heaters (not shown) incorporated (e.g. adhered) to SME 68. Using either method, in the example shown by FIGS. 2A and 2B, the electrical current is supplied to heat SME 68 via electrical leads 71 and 73 that are included in SME 68, or located in proximity to SME 68. As seen leads 71 and 73 are coupled via electrical wiring 75 running through tubular member 60 to a socket 77 in handle 62, to receive electrical supply from console 50 via cable 33. A switch 79 on handle 62 enables physician 56 to switch the electrical current "on" and "off."

The example illustrations shown in FIGS. 2A and 2B are chosen purely for the sake of conceptual clarity. FIG. 2 shows only parts relevant to embodiments of the present invention. For example, other elements included in tool 21, such as magnetic sensor 32, are omitted.

Figure 3:
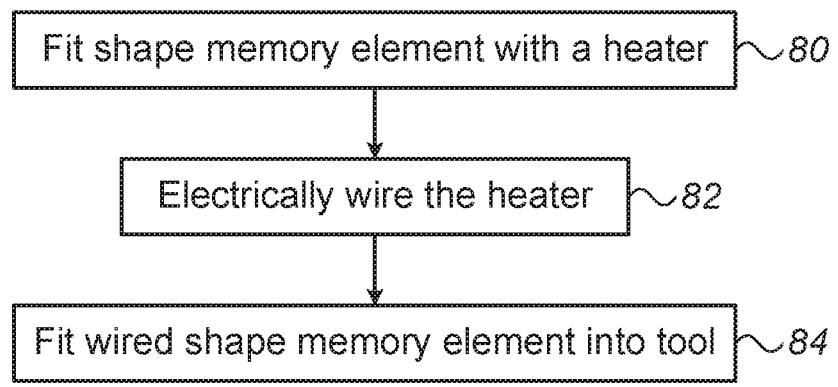
FIG. 3 is a flow chart that schematically illustrates a manufacturing method of the rigid tool of FIG. 2, in accordance with an embodiment of the present invention.

FIG. 3 is a flow chart that schematically illustrates a manufacturing method of the rigid tool of FIG. 2, in accordance with an embodiment of the present invention. The process begins with fitting SME 68 with a heating mechanism, such as a heater, at a heating mechanism fitting step 80. Next, at a wiring step 82, the heating mechanism is electrically wired, so that electrical current can be provided to heat SME 68. Finally, wired SME 68 is fitted to tool 21, at an SME fitting step 84.

The manufacturing process shown in FIG. 3 is brought by way of example, to conceptually describe the process. Other steps or alternative manufacturing steps may take place. For example, tool 21 may already be fully wired and, upon being fitted to tool 21, SME 68 may be electrically connected using electrical sockets.

Figure 4:
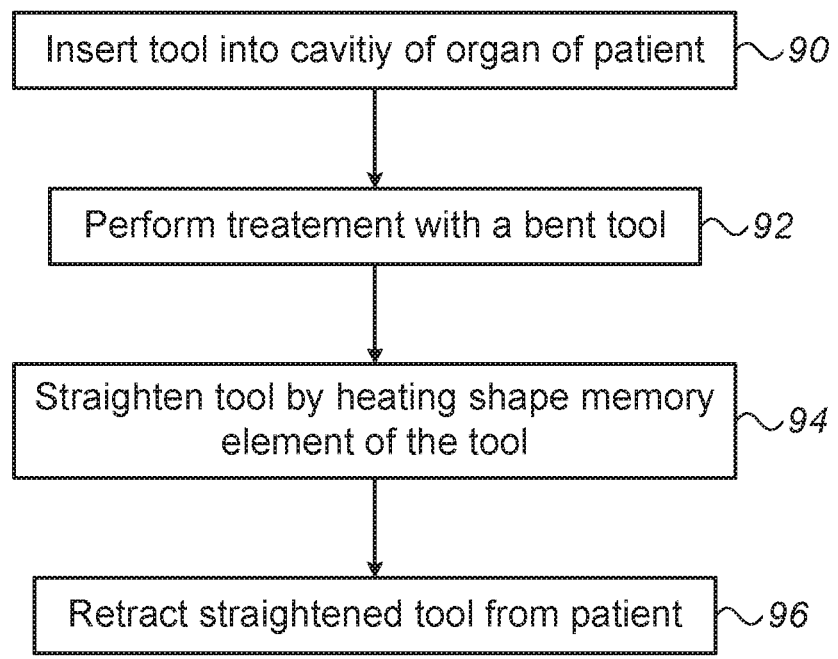
FIG. 4 is a flow chart that schematically illustrates a method for straightening the rigid tool of FIG. 2, in accordance with an embodiment of the present invention.

FIG. 4 is a flow chart that schematically illustrates a method for straightening the rigid tool of FIG. 2, in accordance with an embodiment of the present invention. The process begins with physician 54 inserting tool 21 into an organ, such as a sinus, of patient 34, in a tool insertion step 90. At a treatment step 92, physician 54 manipulates tool 21, including bending suction tip 65, which bendable SME 68 allows, being flexible enough below its heated temperature. When physician 54 needs to straighten tool 21 to retract it, at a straightening tool step 94, the physician commands heating SME 68 to straighten SME 68 into its pre-formed shape 70b, and, by doing so, straightens member 60, as shown in FIG. 2B. Finally, at a tool retraction step 96, physician 54 retracts straightened tool 21 from patient 34.

Although the embodiments described herein mainly address ENT applications, the methods and systems described herein can also be used in other applications.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical tool, comprising:
    (a) a handle;
    (b) a tubular member, attached to and extending from the handle to a distal tip and configured to be inserted into an orifice of a patient, the tubular member having a malleable distal-end section that is configured to be bent so as to perform a medical procedure in the orifice, wherein the distal-end section defines a longitudinal axis, the tubular member having a first length defined between the handle and the distal tip; and
    (c) a bendable shape memory element (SME) coupled to the distal-end section of the tubular member and having a second length smaller than the first length of the tubular member, wherein the SME is configured to straighten when heated into a pre-formed shape, thereby straightening the distal-end section, wherein the SME comprises a sleeve made entirely from a shape-memory material whose pre-formed shape straightens the SME, wherein the sleeve surrounds the longitudinal axis of the distal-end section, wherein the SME is configured to be manually bent via application of an external force to the distal-end section of the tubular member by a user in the absence of heating, wherein the SME is configured to receive an electrical current via wiring running through the tubular member and to be straightened in response to the electrical current.

2. The medical tool according to claim 1, wherein the shape-memory material comprises Nitinol.

3. The medical tool according to claim 1, wherein the SME is configured to be heated by conducting the electrical current provided thereto, so as to revert to the straightened pre-formed shape.

4. The medical tool according to claim 1, and comprising a heater, which is thermally coupled to the SME, and which is configured to be heated by conducting the electrical current provided thereto, so as to straighten the SME to the straightened pre-formed shape.

5. The medical tool according to claim 1, wherein the SME is adhered to an interior or exterior of a wall of the tubular member.

6. The medical tool according to claim 1, wherein the SME is incorporated into a wall of the tubular member.

7. The medical tool according to claim 1, wherein the sleeve is configured to surround the distal-end section.

8. The medical tool according to claim 1, wherein the SME is disposed on an inner or outer surface of the tubular member.

9. The medical tool according to claim 1, wherein the tubular member is sized and configured to be inserted into an orifice of at least one of an ear, nose, or throat of the patient.

10. The medical tool according to claim 1, wherein the distal-end section includes a suction tip, wherein the tubular member includes a lumen, wherein the lumen is configured to cooperate with the suction tip to drain fluid from the patient.

11. The medical tool according to claim 1, wherein the distal-end section is configured to be manually bent by the user from a straight state to a bent state, wherein the distal-end section is configured to be straightened by the SME from the bent state to the straight state in response to heating of the SME.

12. The medical tool according to claim 1, wherein the longitudinal axis defines at least one plane, wherein the sleeve is symmetric about the at least one plane.

13. The medical tool according to claim 1, wherein the sleeve includes a solid cylindrical sidewall.

14. An ear, nose, and throat (ENT) tool, comprising:
(a) a base;
(b) a tubular member extending distally from the base to a distal tip, wherein the tubular member is configured to be inserted into an orifice of at least one of an ear, nose, or throat of a patient, wherein the tubular member includes a distal-end section, wherein the distal-end section is malleable such that the distal-end section is configured to be manually bent by a user from a straight state to a bent state, the tubular member having a first length defined between the base and the distal tip; and
(c) a bendable shape memory element (SME) coupled to the distal-end section of the tubular member and having a second length smaller than the first length of the tubular member, wherein the SME is configured to straighten the distal-end section from the bent state to the straight state in response to heating of the SME, wherein the SME is configured to be manually bent together with the distal-end section in response to the distal-end section being manually bent by the user from the straight state to the bent state, wherein the SME is configured to be resistively heated via passage of an electrical current through the SME from electrical wiring running through the tubular member.

15. The ENT tool according to claim 14, wherein the distal-end section is configured to be manually bent by the user from the straight state to the bent state while the distal-end section is positioned within the at least one of an ear, nose, or throat of the patient.

16. The ENT tool according to claim 15, wherein the SME is configured to straighten the distal-end section from the bent state to the straight state in response to heating of the SME while the distal-end section is positioned within the at least one of an ear, nose, or throat of the patient.

17. The ENT tool according to claim 16, wherein the distal-end section is configured to remain in the straight state while the distal-end section is retracted from the at least one of an ear, nose, or throat of the patient.

18. An ear, nose, and throat (ENT) tool, comprising:
(a) a base;
(b) a tubular member extending distally from the base to a distal tip, wherein the tubular member is configured to be inserted into an orifice of at least one of an ear, nose, or throat of a patient, wherein the tubular member includes a distal-end section that is configured to be bent so as to perform a medical procedure in the orifice, wherein the distal-end section defines a longitudinal axis, wherein the tubular member includes a lumen, the tubular member having a first length defined between the base and the distal tip; and
(c) a bendable shape memory element (SME) coupled to the distal-end section of the tubular member and having a second length smaller than the first length of the tubular member, wherein the SME comprises a shape-memory material, wherein the shape-memory material continuously surrounds the longitudinal axis of the distal-end section, wherein the SME is configured to be manually bent together with the distal-end section via application of an external force to the distal-end section of the tubular member by a user in the absence of heating, wherein the SME is disposed on an outer surface of the tubular member.

19. The ENT tool according to claim 18, wherein the SME is configured as a single unitary piece comprising the shape-memory material.

20. The ENT tool according to claim 18, wherein the SME is configured to be resistively heated via passage of an electrical current through the SME from electrical wiring running through the tubular member, so as to revert to a straightened pre-formed shape.

* * * * *